(12) United States Patent
Hargrave et al.

(10) Patent No.: US 7,942,840 B2
(45) Date of Patent: May 17, 2011

(54) FRACTURE BRACE

(75) Inventors: David C. Hargrave, Madison, NJ (US); Eugene Prais, West Milford, NJ (US)

(73) Assignee: DJO, LLC, Vista, CA (US)

( * ) Notice: Subject to any disclaimer, the term of this patent is extended or adjusted under 35 U.S.C. 154(b) by 1037 days.

(21) Appl. No.: 11/051,791

(22) Filed: Feb. 3, 2005

(65) Prior Publication Data

US 2006/0052730 A1    Mar. 9, 2006

Related U.S. Application Data

(60) Provisional application No. 60/607,704, filed on Sep. 7, 2004.

(51) Int. Cl.
A61F 5/00 (2006.01)
A61F 5/37 (2006.01)
A41D 13/08 (2006.01)

(52) U.S. Cl. .................... 602/21; 602/13; 602/5; 602/1; 128/878; 128/879; 2/455; 2/16

(58) Field of Classification Search .............. 602/12, 602/13, 20–22; 2/16, 22, 24; 128/878–879, 128/DIG. 20
See application file for complete search history.

(56) References Cited

U.S. PATENT DOCUMENTS

| | | | |
|---|---|---|---|
| 4,382,439 A * | 5/1983 | Shen ........................... 602/22 |
| 4,441,490 A | 4/1984 | Nirschl | |
| 4,441,493 A | 4/1984 | Nirschl | |
| 4,654,893 A | 4/1987 | Meyers et al. | |
| 4,662,364 A | 5/1987 | Viegas et al. | |
| 4,788,972 A * | 12/1988 | DeBusk ........................... 602/5 |
| 4,796,611 A | 1/1989 | Wardlaw | |
| 4,881,533 A | 11/1989 | Teurlings | |
| 5,160,314 A | 11/1992 | Peters | |
| 5,254,078 A | 10/1993 | Carter et al. | |
| 5,279,545 A | 1/1994 | Reese, Sr. | |
| 5,383,844 A | 1/1995 | Munoz et al. | |
| 5,399,152 A | 3/1995 | Habermeyer et al. | |
| 5,415,624 A | 5/1995 | Williams | |
| D371,845 S | 7/1996 | Varn | |
| 5,577,998 A | 11/1996 | Johnson, Jr. et al. | |
| 5,672,150 A | 9/1997 | Cox | |
| 5,713,837 A | 2/1998 | Grim et al. | |
| 5,722,092 A | 3/1998 | Borzecki et al. | |
| 5,733,249 A | 3/1998 | Katzin et al. | |
| 5,749,841 A | 5/1998 | Moore | |
| 5,772,620 A | 6/1998 | Szlema et al. | |
| 5,954,676 A * | 9/1999 | Kramer, III ....................... 602/6 |
| 6,024,715 A | 2/2000 | Maxwell | |

(Continued)

FOREIGN PATENT DOCUMENTS

FR    1 482 514    6/1966

(Continued)

Primary Examiner — Patricia M Bianco
Assistant Examiner — Tarla R Patel
(74) Attorney, Agent, or Firm — Ropes & Gray LLP

(57) ABSTRACT

Braces are disclosed that are capable of stabilizing an injured limb, particularly an injured wrist. An exemplary brace fits across the injury in contact with the user's hand or foot and, in certain embodiments, in contact with the thumb and/or fingers or toes. The brace typically contains an adjustable casing and in some embodiments a removable support connecting one portion of the user's arm to another. The brace also includes compressible material such as an air cell. Systems and method for use and manufacture of the braces are also contemplated.

37 Claims, 13 Drawing Sheets

U.S. PATENT DOCUMENTS

| | | |
|---|---|---|
| 6,106,492 A | 8/2000 | Darcey |
| 6,142,966 A | 11/2000 | Hely |
| 6,146,347 A | 11/2000 | Porrata |
| 6,146,348 A | 11/2000 | Slautterback |
| 6,186,966 B1 | 2/2001 | Grim et al. |
| 6,293,918 B1 | 9/2001 | Wang |
| 6,328,706 B1 | 12/2001 | Yattavong |
| 6,443,918 B1 | 9/2002 | Wang |
| D477,088 S | 7/2003 | Brown et al. |
| 6,592,538 B1 | 7/2003 | Hotchkiss et al. |
| 6,692,453 B2 | 2/2004 | Wolfe |
| 6,740,056 B2 | 5/2004 | Slautterback |
| 6,866,646 B2 * | 3/2005 | Hopkins et al. ............ 602/5 |
| 7,033,331 B1 | 4/2006 | Hely |
| 7,048,703 B2 | 5/2006 | Riach |
| 7,288,076 B2 | 10/2007 | Grim et al. |
| 2002/0002348 A1 | 1/2002 | Wiggins et al. |
| 2003/0139695 A1 | 7/2003 | Riach |
| 2004/0019306 A1 | 1/2004 | Brewer |
| 2004/0039315 A1 | 2/2004 | Goumas |
| 2004/0049141 A1 * | 3/2004 | Slautterback et al. ......... 602/21 |
| 2004/0092853 A1 * | 5/2004 | Degun et al. .................. 602/27 |
| 2004/0133137 A1 | 7/2004 | Hargis et al. |
| 2004/0143205 A1 | 7/2004 | Ressel |
| 2004/0147862 A1 | 7/2004 | Chen et al. |
| 2004/0176714 A1 | 9/2004 | Darcey |
| 2005/0096575 A1 | 5/2005 | Weaver |
| 2005/0197609 A1 | 9/2005 | Mills |

FOREIGN PATENT DOCUMENTS

| | | |
|---|---|---|
| WO | WO-2006/028489 | 3/2006 |

* cited by examiner

FRACTURE BRACE

PRIORITY INFORMATION

This application claims the benefit of U.S. Provisional Application No. 60/607,704, filed Sep. 7, 2004, the specification of which is incorporated by reference herein.

BACKGROUND

Injuries to the limbs, particularly to the hands, arms and wrist, are commonly treated by the use of a cast or other brace that supports the injured limb and, in certain cases, prevents the limb from rotating around the wrist or other applicable joint. These injuries include sprains, fractures, contusions and other injuries that are common and frequent and, unless properly treated, recurrent.

Certain injuries, particularly limb fractures, result in the limb becoming misaligned with respect to its normal position. This effect may be seen, for example, in an open wrist fracture where radial bones puncture and protrude through the skin and result in the broken radius becoming further bent or otherwise deformed. To treat such a fracture, the physician must appropriately align the fractured limb then apply a support suitable to stabilize the limb during healing. The process of properly aligning and stabilizing a fractured limb to begin healing is known as "reduction" of the fracture. Braces commonly used to maintain reduction of a fracture or otherwise treat an injured limb include plaster casts prepared by a physician and applied by forming the plaster about the patient's limb. In time, the plaster will harden, leaving the limb compressed within a rigid cast. Such braces, although generally effective, cause discomfort and other problems for the patient. For example, a typical compression cast is not adjustable, and therefore its position on the limb is fixed upon compression. This compression may be applied too tightly for some patients; it also may become too loosely attached over time as swelling in the arm recedes.

Thus, it is desirable to have a brace that allows greater flexibility in the function of the brace while still providing adequate support for the injured limb, particularly in the treatment of limb fractures.

SUMMARY OF THE INVENTION

The braces described herein are, among other things, capable of stabilizing an injured limb, and in one particular embodiment, an injured wrist. In certain cases the brace substantially immobilizes the injured limb. The braces are suitable for treatment of injuries arising from fracture, sprain, contusion, or other injuries to the limb. An exemplary brace fits across the injured limb (e.g., across the injured wrist). The brace may be fitted in contact with the user's limb (e.g. a hand) or other appendage and, in certain embodiments, in contact with the thumb and/or fingers, with the foot and/or toes, etc. The braces are adjustable and may have components sufficiently adapted to impede the flexion of a limb and, in certain embodiments the deviation, extension, inversion and/or eversion thereof.

A brace optionally contains an adjustable casing, thereby allowing the patient or treating physician to tighten or loosen the brace to achieve desired support. In certain embodiments the brace comprises two pieces joined by a support. One piece may be disposed about one portion of the patient's limb and the other piece may be disposed at another portion. The support connects between two pieces, thereby joining one portion of the user's limb (e.g., the forearm) to another (e.g., the user's upper arm). A brace also includes compressible material at least partially enclosed by the casing. Methods for use and manufacture of the braces are also contemplated.

In certain embodiments a brace comprises an adjustable caging fitted to the injured limb and having at least one component adapted to impede flexion of the injured limb, and compressible material at least partially enclosed by the adjustable casing. The adjustable casing may be adapted to fit across a user's injured wrist and in contact with the user's hand. It may also be adapted to fit across a user's injured ankle, or other limbs or appendages. The brace may have at least one component that is adapted to impede palmar flexion, dorsi flexion, radial deviation, and ulnar deviation of the user's wrist. A brace may also have at least one component adapted to impede inversion, eversion, plantar flexion and dorsal flexion of a user's ankle. In certain embodiments a brace may impede one or more of the foregoing motions without impeding pronation or supination of the user's forearm or lower leg.

An adjustable casing may surround the user's thumb or abut at least a portion of the user's thumb.

The brace may also have a mechanical fastener for tightening and loosening the casing. In certain embodiments the adjustable casing is a stiff shell. In certain embodiments the casing is flexible in one or more dimensions, for example in a dimension transverse to the radius, in a dimension longitudinal with respect to the radius, or both. Such a flexible casing may also have a strengthening component that extends in a selected dimension along the casing.

As noted, compressible material is used. In certain embodiments the compressible material comprises at least one air cell or a foam pad. Where at least one air cell is used, the brace may be adapted to allow the user to control the pressure or the distribution of the air in the at least one cell. In certain embodiments, the compressible material provides for contoured loading (e.g., an air cell with perimeter loading). The compressible material may contain one or more surfaces or surface sections that contact the injured limb (such as in the vicinity of the fracture or other injury) while other surfaces or surface sections of the material do not contact the limb. In this respect, the material may be adapted to apply supporting pressure at selected levels and at selected locations along the limb.

The at least one air cell may include a valve for allowing a user to selectively inflate and deflate the at least one air cell. An electrical or a manual pump may also be provided for adjusting the pressure of the air in the cell. An air cell may be quilted or dimpled to compartmentalize the air into subcells, the quilting serving to impede the subcells from expanding. In wrist brace embodiments, a hand-held component may be included for gripping by the user, the use of which may allow the user to adjust the distribution and/or pressure of the air in the cell. The at least one air cell may be adapted to provide pulsating pneumatic compression to a user's wrist as the user flexes the hand.

In certain embodiments a support is used (e.g., a rod, hinge, joint, spring, etc.) to impede (and, in certain embodiments, substantially prohibit) movement of the injured limb. The support may connect a user's forearm to the user's upper arm, a user's foot to the user's leg, etc. In certain embodiments the support is removable and reattachable by the user.

The brace may also have a liner for absorbing moisture positioned between a user's limb and the adjustable casing. The liner may be wicking material or foam, for example.

The brace may have at least one component adapted to allow the user to be treated with cryotherapy without removing the brace. The brace may have at least one perforation in the casing for allowing ambient air to contact the injured limb to ventilate the injured limb. The brace may also have a component adapted to allow a cooling agent to be placed in contact with the injured limb.

Methods of use and manufacture are also envisioned. For example, a method may be adapted for treating an injured limb, comprising providing compressible material that is at least partially enclosed in an adjustable casing, the adjustable casing having at least one component adapted to impede flexion of the injured limb, and fitting the casing to the injured limb.

The methods are applicable to any limb injuries. For example, the methods may apply to a broken wrist or a broken ankle.

BRIEF DESCRIPTION OF THE DRAWINGS

The foregoing and other objects and advantages of the invention will be appreciated more fully from the following further description thereof, with reference to the accompanying drawings wherein.

DESCRIPTION OF CERTAIN ILLUSTRATED EMBODIMENTS

The device and methods described herein provide for braces and methods for bracing an injured limb. To provide an overall understanding of the invention, certain illustrative embodiments are herein described, as more particularly set forth in the figures. However, it will be understood by one of ordinary skill in the art that the systems and methods described herein can be adapted and modified for other suitable applications, and that such other additions and modifications will not depart from the scope hereof. For example, representative embodiments may be applied to injuries to the forearm, the wrist, hand, fingers, the upper arm, injuries to the leg, or ankle, or to bones of any or all of the foregoing.

Figure 1:
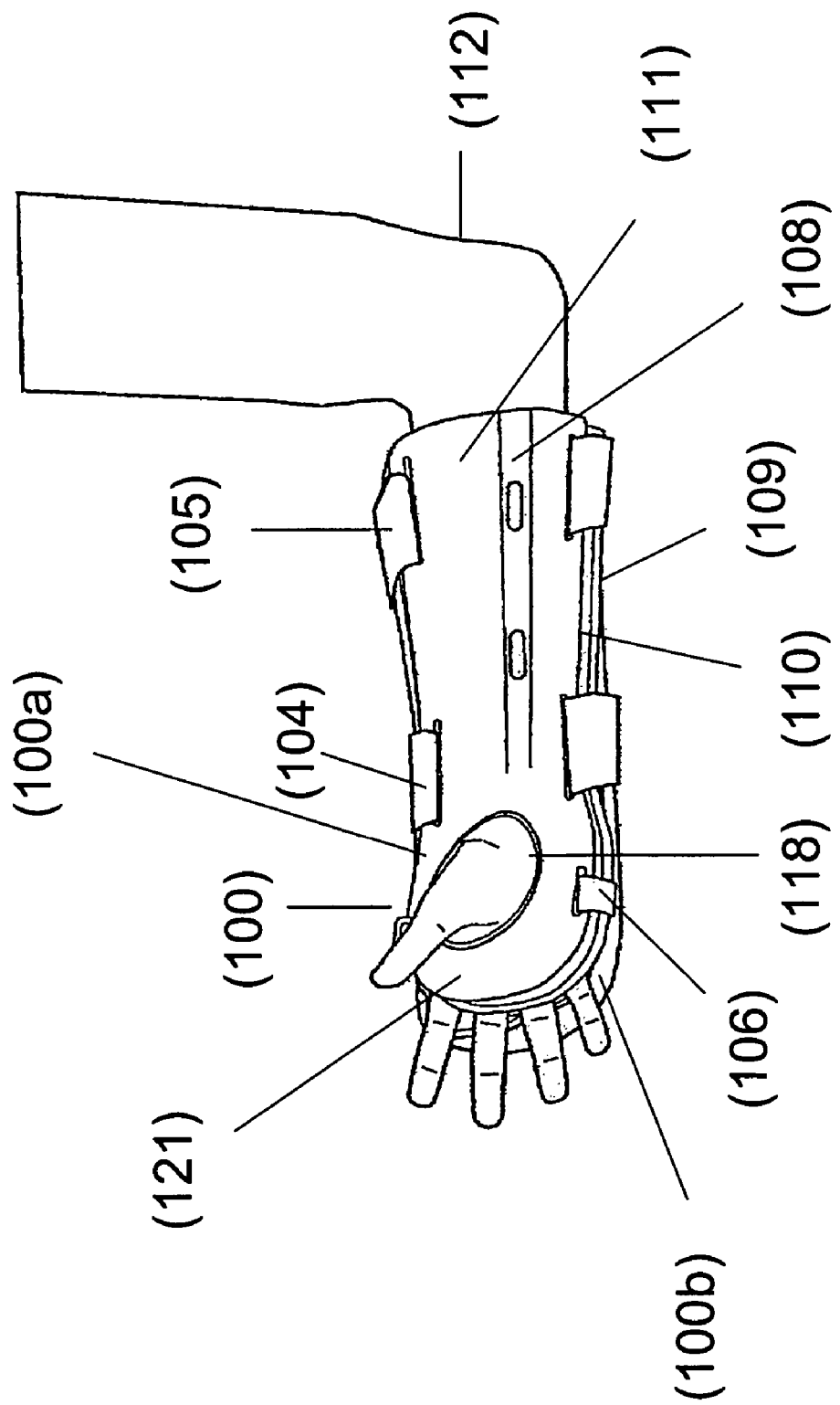
FIG. 1 depicts an embodiment of a brace attached to a user's arm.

FIG. 1 depicts an embodiment of a brace (100), including a casing (111) having medial (100a) and lateral (100b) portions, the brace (100) being fitted to a limb (112). A portion of the depicted brace (121) surrounds the thumb and supports the fingers, while the thumb extends through a hole (118). Also shown is a liner (109), compressible material (110) at least partially enclosed by the casing (111), and a slot (108) affixed to the casing (111) for reception of an arm bracket (not shown). The brace may be secured to a user's limb (112) by one or more straps. FIG. 1, depicts a brace secured to a user's arm by a mid strap (104), a proximal strap (105), and a distal strap (106).

In practice, the brace (106) fits across the injured limb (112). It may also be fitted in contact with the user's hand, foot, etc. In certain embodiments, the brace is adapted to fit in contact with the thumb, fingers, or both. In certain embodiments, the brace is adapted to fit against the palm of the hand, the back of the hand, or both. In certain embodiments the compressible material (110) is positioned on the lateral side of an arm, on the medial side of an arm, or both.

The braces, such as brace (100), typically contain at least one casing (111), which may partially or completely enclose the compressible material. In certain embodiments the casing is rigid. Rigid casing embodiments include, for example, a stiff shell. Any suitable stiffening material may be used, such as high density polymer, aluminum, etc.

Figure 2:
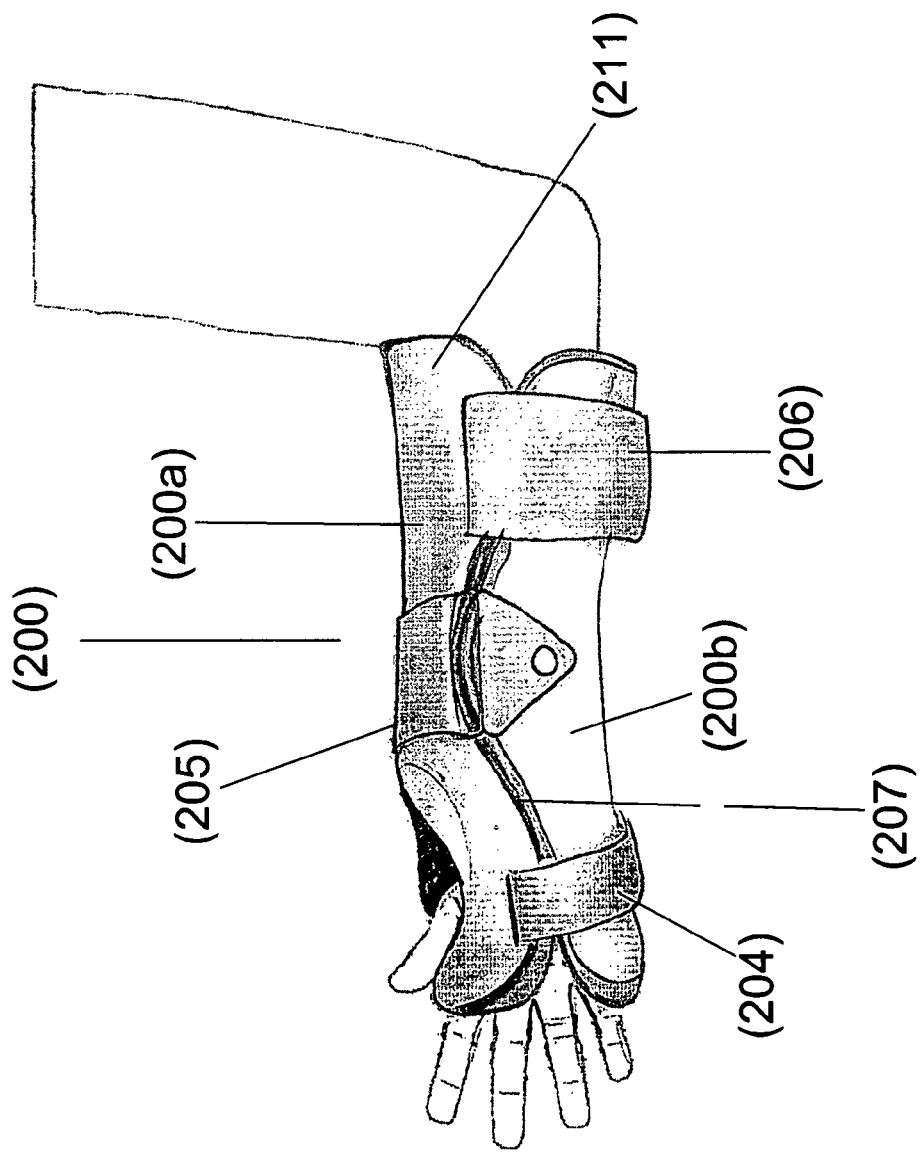
FIG. 2 depicts an embodiment of a brace having interlocking shells in the casing.

In other embodiments the casing has one or more flexible components. An exemplary embodiment of such a casing is shown in FIG. 2. Brace (200) has a casing (211) with both dorsal (200a) and volar (200b) shells, and straps (204, 205, and 206). When fully assembled, the shells are interlocked along a seam (207), which allows the dorsal shell to envelope the fracture location. The dorsal shell and, in certain embodiments, the volar shell is made from flexible material, such as low density polyethylene, which allows the brace to conform to the injured limb as the straps are tightened. Any suitable flexible material may be used. Exemplary flexible materials may include low density polymer, such as low density polyethylene, or denim, canvas, etc.

In certain other embodiments the casing has both flexible and stiff components. For example, the casing may be flexible in a transverse direction across the limb and may also contain one or more components that stiffen the casing in the dimension longitudinal with the limb. Flexible casings and flexible casing components allow the casing to be anatomically formed, being adapted to be flexible with respect to the limb and, when tightened, capable of supporting or even immobilizing the limb.

As noted, an exemplary brace is typically adjustable, such as by the straps shown in FIG. 1 and/or FIG. 2, and is typically fitted to a limb, thereby allowing the user to tighten the brace as necessary to achieve desired support. The casing may contain straps, buckles, laces, or other suitable mechanical structures for this purpose. The straps may be of flexible elastic or non-elastic material. The straps, etc. may assist in stabilizing or even immobilizing the injured limb. For example, VELCRO® straps may be used to secure a casing such as (111) or (211) to an injured limb.

Furthermore, the straps, etc. may allow the braces (100) and (200) to be removed and re-attached as desired by the patient or physician. In one aspect, an adjustable casing (211) enables the user to tighten the casing during its initial placement on the arm as necessary to support the injury, while avoiding over-compression that often results when a typical plaster cast is used. In another aspect, the adjustability feature may assist in managing swelling in the vicinity of an injury. As swelling recedes during the course of healing, the adjustable casing allows the user to tighten the brace in response, thereby further pushing swelling fluid away from the site of the injury. This process is known as "milking the edema."

In another aspect, a brace such as (100) and (200) may be removed by the user to expose the injured arm for a physician check-up, for taking X-rays, or any other reason, and it may be placed again on the injured arm when desired. In certain embodiments a brace such as (100) and (200) may be constructed from radiolucent material to permit a physician or technician to perform shadowless X-ray on the injury without removal of the brace.

Figure 3:
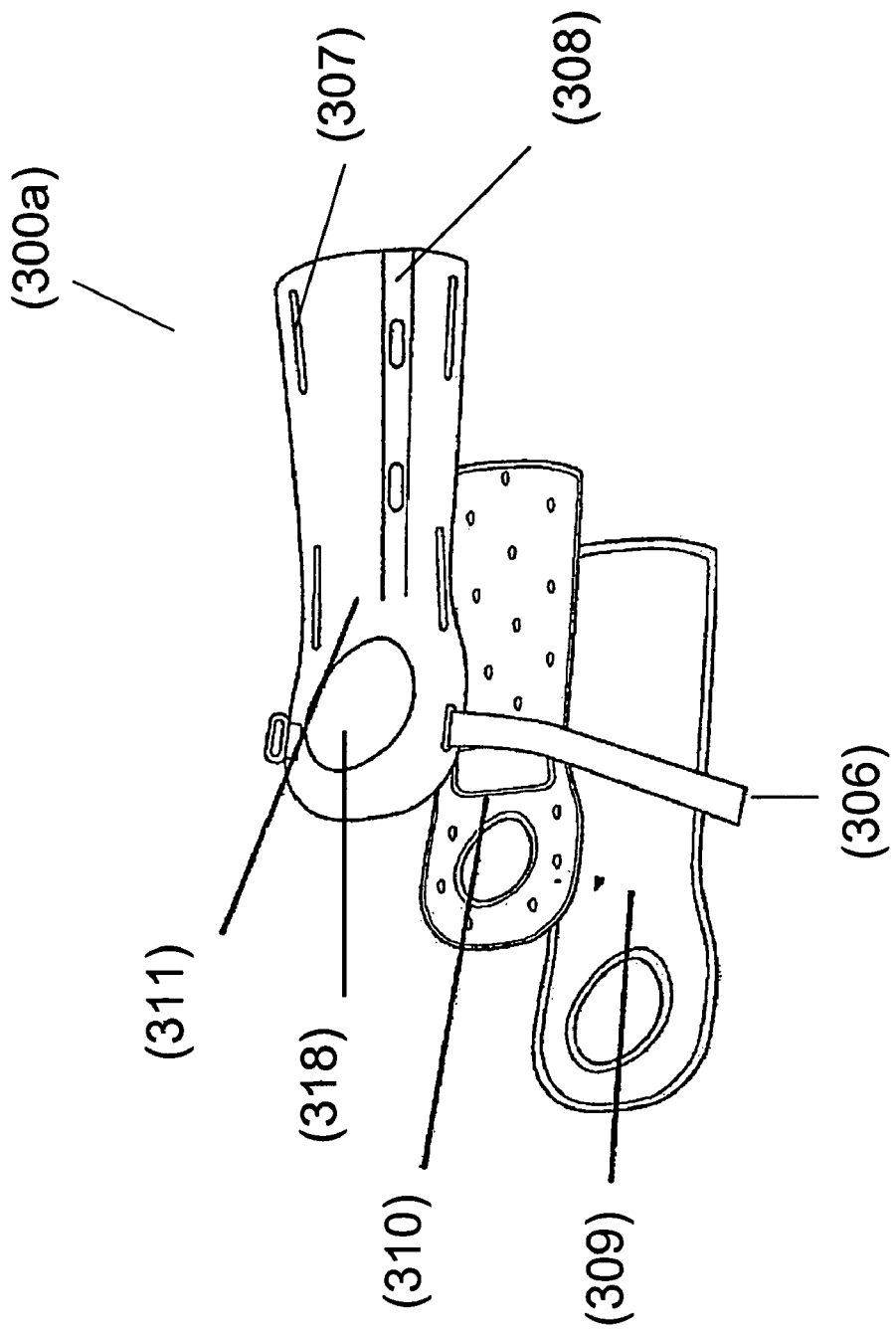
FIG. 3 depicts an embodiment of a medial support for a brace.
Figure 4:
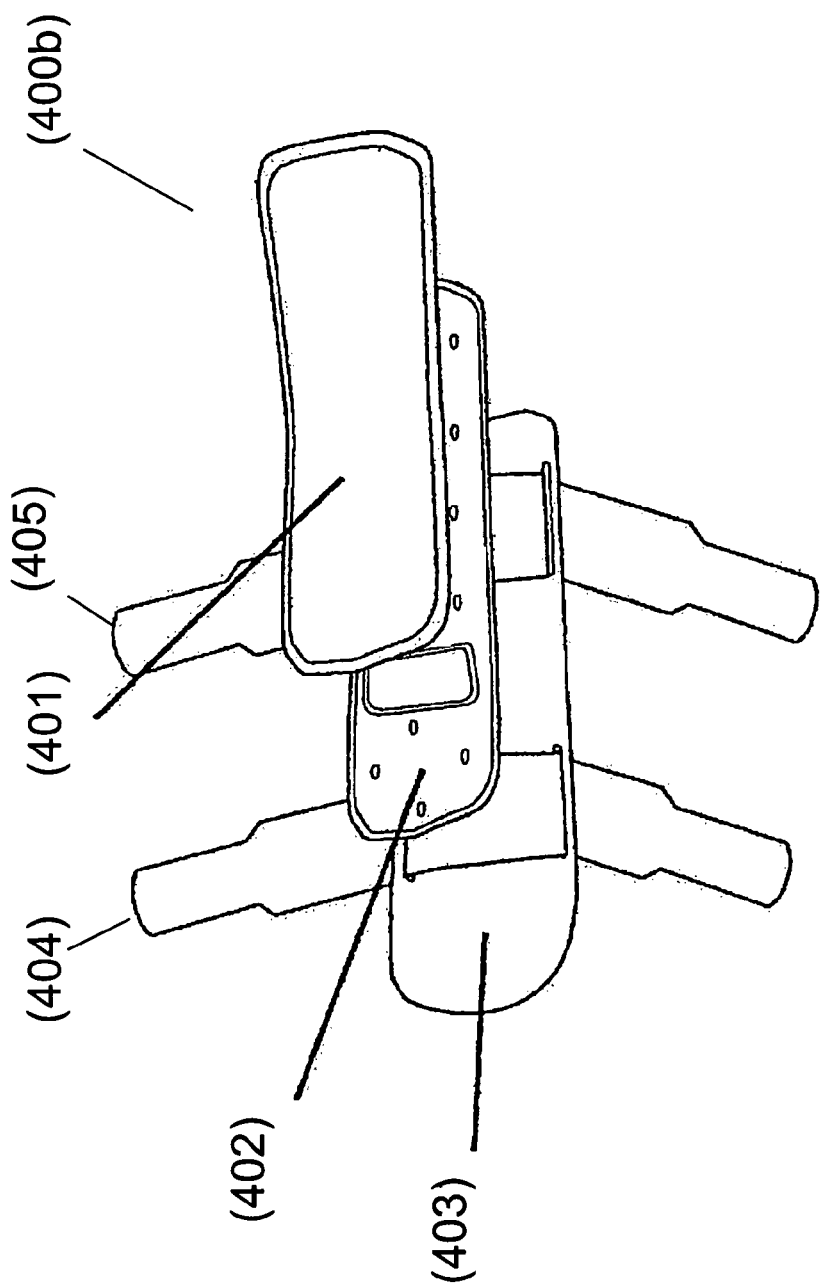
FIG. 4 depicts an embodiment of a lateral support for a brace.

In certain embodiments the braces are assembled from multiple components. FIG. 3 depicts an exploded view of a medial component (300a) of a brace (300), including a casing (311) having perforations (307) for ventilation, a thumb slot (318), and a distal strap (306). Also shown is a liner (309), compressible material such as an air cell (310) at least partially enclosed by the casing (311), and a slot (308) affixed to the casing (311). The medial component (300) may be fitted to the limb and, in certain embodiments, fitted to a lateral component as shown in FIG. 4. Depicted is an exploded view of a lateral portion (400b) of a brace (400) having a casing (403), a liner (401), and compressible material such as an air cell (402) at least partially enclosed by the casing (403). Also shown is a mid strap (404) and a proximal strap (405), which allows a brace to be adjusted as desired by the user or a physician.

The compressible materials depicted in FIGS. 1-4 may include air cells, which are bags filled with air. The bags are typically flexible. Although air cells are depicted, those skilled in the art will recognize that any suitable compressible material may be employed. In certain embodiments the compressible material includes a pad. Typical pads may include rubber, thick fabric, foam, or any other suitable compressible material. Multiple pads or other compressible material items may be used. The compressible material may be partially or fully enclosed by a casing.

Figure 5:
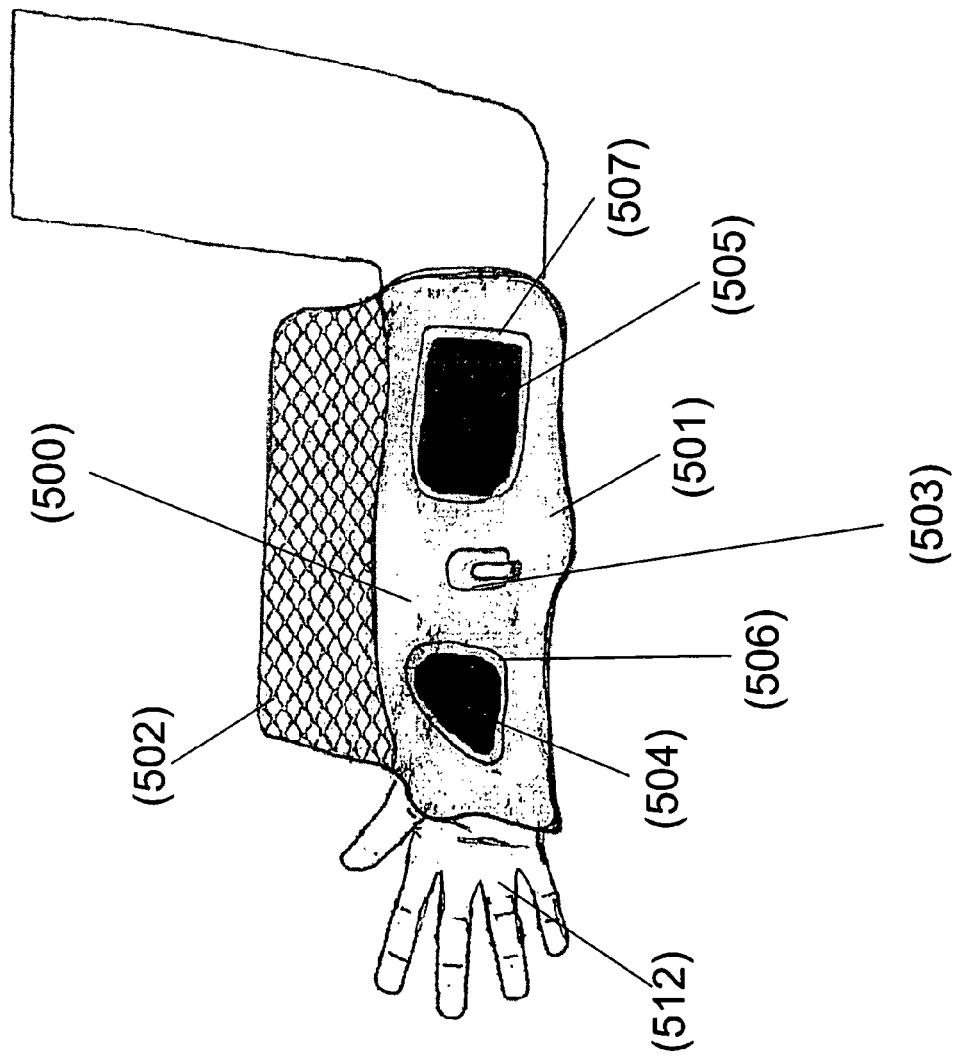
FIG. 5 depicts an embodiment of a portion of a brace containing an air cell.

In certain embodiments, the compressible material is shaped, sized, and/or positioned to provide customized support to selected locations along the limb. Such support is also known as "contoured support." FIG. 5 depicts a surface view of a perimeter air cell (500), which is an optional embodiment of the compressible material (310) shown in FIG. 3, as may be suitable for application to provide contoured support for a limb (512). Also depicted is an outer shell (502), and a valve (503) for filling and deflating the air cell. In this embodiments, the outer shell (502) and air cell would extend beyond the base of the thumb so as to impede the rotation of the wrist, but not to prohibit the flexing of the thumb.

The depicted air cell (500) has an air compartment (501) with two pockets (504 and 505) interspersed therein, the pockets having inner walls (506 and 507, respectively) that separate the pockets from the remainder of the air compartment. In this embodiment, air can flow within the compartment (501) but not within the inner pockets (504 and 505). The air cell is sized and shaped for controlling the amount and/or distribution of supporting pressure applied to selected locations on the limb.

The inner pockets (504 and/or 505) may be inflexible, such as by having an external stiff surface; they may also be stretchable. They may also be separated from the compartment by stitching, gluing, etc. In the depicted embodiment, the inner pockets (504 and/or 505) do not expand significantly when the air cell is inflated. In such an embodiment, the air cell (500) may be positioned on the limb such that the non-expanding inner pockets (504 and/or 505) form a protective pocket directly above the injury site. In this respect, the compartment (501) may be fitted in contact with the injured limb in the vicinity of the injury site, while leaving the surface above the injury free from contact with the limb. In this embodiment the air cell (500) may be adapted so that supporting air pressure is applied at selected levels and to selected locations (such as around the perimeter of the compartment) along the limb.

In certain embodiments, suitable compressible material, such as the air cell depicted in FIG. 5, may be quilted, dimpled, or otherwise adapted to provide compartmental air pockets with reduced or no fluid communication there between. Air cells with compartmentalized air pockets may be fashioned to be less expandable than pockets with little or no compartmentalization, and compartmentalizing the pockets provides the user with the ability to control the pressure and/or distribution of the air cell at given points along the limb.

The compressible material, such as an air cell of the type manufactured and sold by the Aircast Inc. of Summit, N.J., has one or more surfaces or compartments adapted to contact the injured limb, such as in the vicinity of the fracture or other injury, and apply a desired supporting pressure to the limb while certain surfaces or compartments of the material do not contact the limb. While an air cell (500) is exemplified in FIG. 5, those skilled in the art will recognize that foam pads or other suitable compressible material may be adapted to provide contoured support to the injured limb. In certain embodiments compressible material may have varied thickness along the material, providing one or more sections that contact the injured limb and one or more sections that have no or little contact therewith. In certain embodiments the compressible material may be adapted to provide pillow-like support under a fracture or other injury site on the limb.

In certain embodiments compressible material has multiple compartments that provide balanced support of an injury along the outer edges of the compressible material. In certain embodiments an air cell may have no compartments, though such embodiments may result in the air cell inflating like a football, leaving the center of the cell as the thickest portion and tapering the air cell to the sides thereof. In such embodiments, when external forces are applied to the outer edges of the air cell, the air may be displaced to the center, and the outer edges may provide less support for the injury than is provided by multi-compartment air cells.

Also shown in FIG. 5, when used, an air cell may contain one or more valves (503) for adjusting the pressure of one or more air pockets in the air cell. An electrical or manual pump (not shown) may also be employed to adjust the pressure of the air cell. In certain embodiments the air pressure of the air cell changes as the user flexes the hand/fingers.

Additionally, in certain embodiments, a hand-held pump component (not shown) may be included with the brace and, when gripped by the user, allows the user to flex the fingers of the user's hand, thereby flexing the muscles in the forearm. Components other than a hand-held pump may be used, such as a ball. The flexing of the forearm may, in turn, provide for a decrease in swelling in the arm. Also known as pulsating pneumatic compression, the process of reducing arm swelling by flexing the forearm may be assisted by this invention, and may help to relieve pain in the patient's arm.

Figure 6:
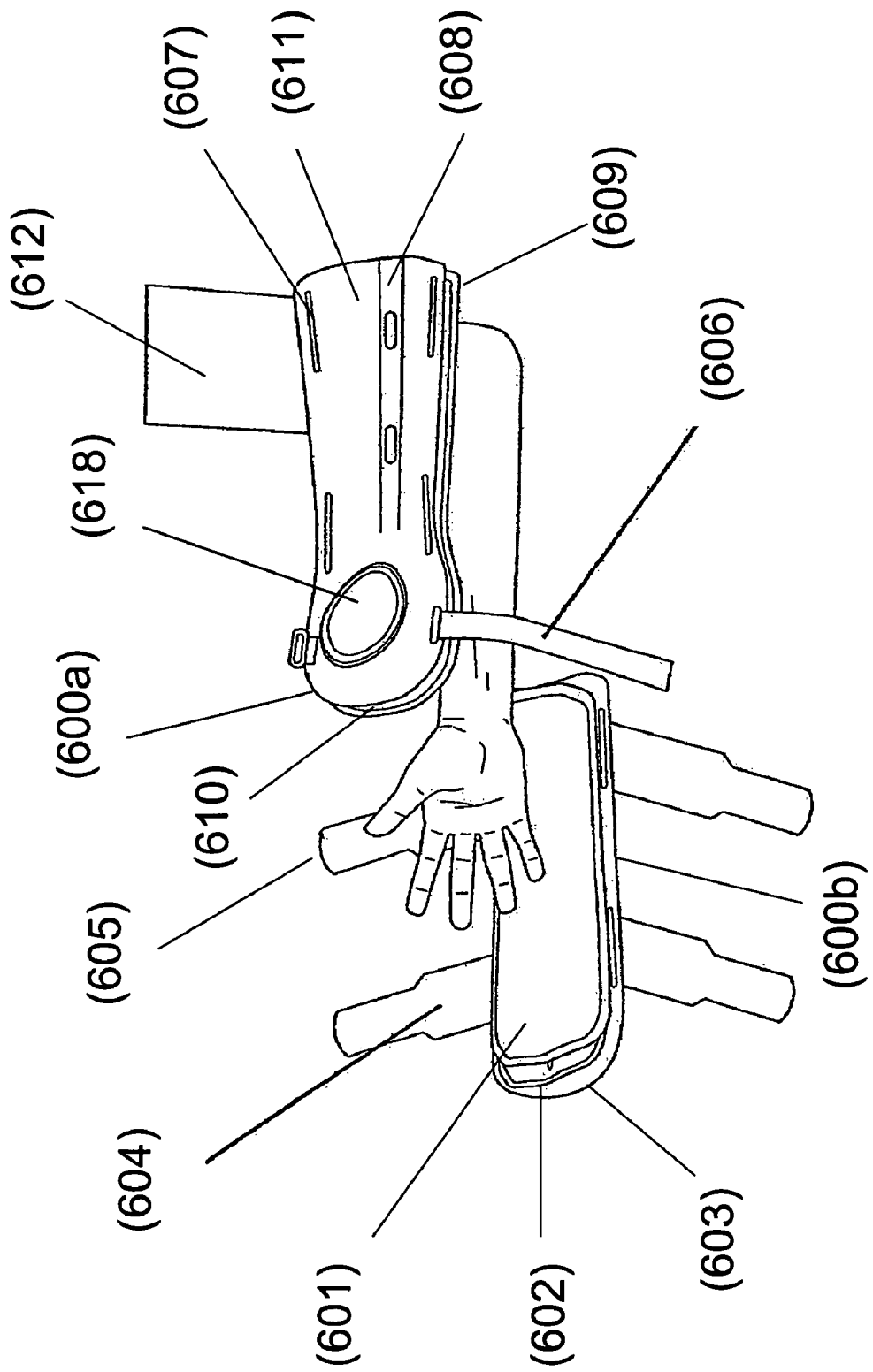
FIG. 6 depicts the application of an exemplary brace to an injured arm.

FIG. 6 depicts an assembly of an embodiment of a brace (600) having medial (600a) and lateral portions (600b), as shown prior to its application to a user's arm (612). The brace includes a casing having medial (611) and lateral (603) portions, and a mid strap (604), a proximal strap (605), and a distal strap (606) for securing the brace (600) to the arm (612). Also shown is a first air cell (610) at least partially enclosed by the medial portion of the casing (611), and a slot (608) affixed to the medial portion of the casing (611), as well as a second air cell (602) at least partially enclosed by the lateral portion of the casing (603).

As noted above, in certain embodiments the brace includes a liner positioned between the user's arm and the remainder of the brace. As shown in FIG. 6, the brace may include a lateral liner (601), a medial liner (609), or both. The liner may be capable of absorbing moisture from the arm. In certain embodiments the liner is fabric (e.g., a wicking material, perforated foam), or it may be any other suitable material. When the brace (600) is applied to a limb, the liner may be adapted to contact the limb and to assist in fitting the casing to the limb. The liner may be positioned in any position (for example, adjacent to the user's arm) to achieve desired comfort and effect. In certain embodiments the brace and its components are made of waterproof material for allowing the brace to be submerged in water.

The brace may also include a perforation (607) for allowing ambient air or other cooling agents to contact the arm or fabric adjacent thereto for ventilation. The air cell may also be adapted to facilitate ventilation and moisture management. For example, the cell may have holes that allow ambient air or cooling agents to contact the arm. In alternative embodiments, the brace may include a bladder filled with liquid (e.g., cold water). Suitable heat-transfer materials (e.g., aluminum) may also be used to form at least a part of the brace and thereby facilitate the ventilation and/or cooling of the arm. In certain embodiments, the brace is adapted to allow the patient to be treated by cryotherapy, preferably without removing the brace.

A brace may have at least one component that extends across the wrist from the forearm to the hand. In certain embodiments the at least one component is included as part or all of the adjustable casing. In certain embodiments the brace includes a component that covers the perimeter of the wrist and/or extends across the wrist into contact with the hand. The brace may have one or more components adapted to impede the wrist from undergoing one or more of palmer flexion, dorsal flexion, radial deviation, and ulnar deviation, and optionally also to impede the pronation and supination of the forearm. Impeding one or more of such motions may include impeding the wrist or forearm from extending in the range of motion enabled by such rotation. In certain embodiments, the brace includes at least one component positioned against the arm and hand so as to impede dorsi flexion, palmar flexion, ulnar deviation and radial deviation of the wrist, without impeding pronation or supination of the forearm. In certain embodiments the brace may have one or more components adapted to impede palmar and dorsi inflection of a wrist but not radial or ulnar deviation, or to impede radial and ulnar deviation but not palmar or dorsi inflection.

The depicted brace is capable of stabilizing the injured arm, particularly an injured wrist, and, in certain embodiments, the brace may immobilize the hand, wrist, fingers, thumb, or any of the foregoing. To this end, the brace may be adapted to impede rotation of the wrist to stabilize a fracture or a sprain. Those skilled in the art recognize, however, that the brace may also be suitable for use to stabilize an arm suffering from carpal tunnel syndrome or from ligament or tendon injuries. In certain embodiments, the brace is adapted to immobilize the wrist, such as by prohibiting rotation of the hand around the wrist joint, but typically does not (although it may) prevent flexing in the fingers and thumb. The brace may immobilize the wrist against palmar flexion, dorsi flexion, radial deviation, and ulnar deviation, and may also immobilize the pronation and supination of the forearm. The brace may, but need not, be adapted to impede the extension and flexion of the arm about the elbow or about the shoulder. The brace may also be adapted as an ankle brace to impede the flexion, deviation, inversion or eversion of an ankle. An ankle brace may have at least one component (e.g., the adjustable casing, a rod or other stiff item, etc.) that allows the brace to impede plantar flexion, dorsal flexion, inversion, and/or eversion of the ankle.

In certain embodiments, a brace may include a stiffening component to stabilize a thumb, finger, toe, or other appendage. As shown below in FIG. 12, a spica composed of aluminum or other suitable metal or polymer may be included with the brace to immobilize an appendage. The stiffening component may be particularly useful in the event of a fracture to the lower hand (e.g., a scaffoid fracture), and it may be removable by the user or physician, as desired. In certain embodiments the stiffening component is adapted to immobilize the injured appendage.

In certain embodiments, a brace may be adapted to treat both a scaffoid fracture and a distal radial fracture.

Figure 7:
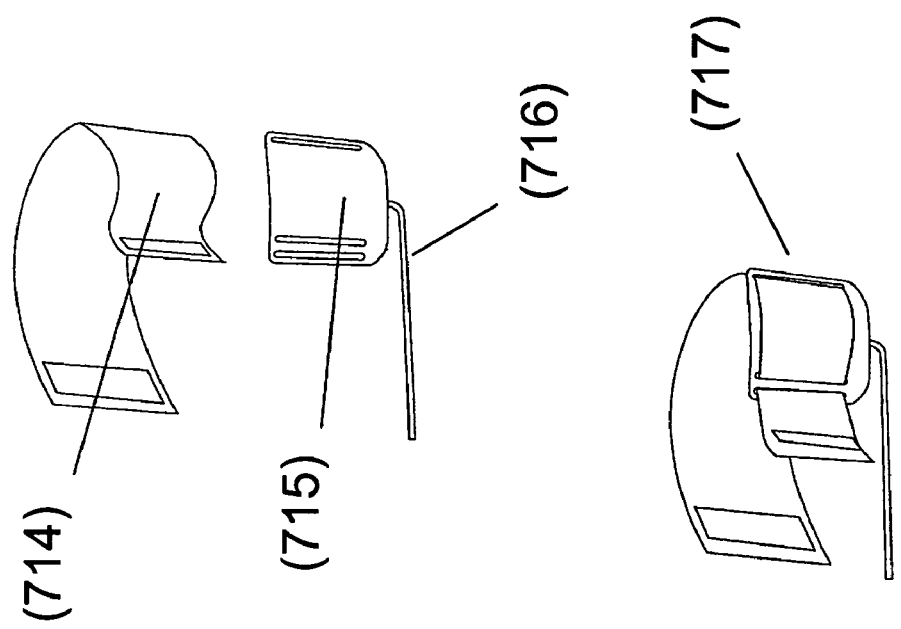
FIG. 7 depicts an embodiment of a removable support for use in connection with a brace.

A brace may also include a support connecting one portion of the user's limb to another to further impede movement of the limb and provide overall stability to the injured limb. For example, a bracket may be used for connecting an upper arm to a wrist brace, thereby impeding the rotation of the forearm around the elbow and further stabilizing the injured arm. In certain embodiments other structures are used to stabilize the arm, such as a hinge, joint or spring connecting the forearm to the upper arm. In certain embodiments, a bracket is used to connect the upper arm to the forearm, such bracket being accompanied in certain embodiments by an arm band that connects the bracket to the upper arm. For example, FIG. 7 depicts an embodiment of a support (717) for connecting one portion of a user's arm to another or may be adapted to stabilize any portion of a limb to another. The support (717) includes a slot (708) for receiving a bracket having plate (715) and rod (716) portions and an arm band (714). The support (717) may be adapted to be removable. Those skilled in the art recognize that similar embodiments are available for legs and ankles.

In certain embodiments the slot (708) and bracket are adapted to allow the user to adjust (and stabilize) the angle between the upper arm and the forearm. The angle may be 90 degrees or any other desired angle. The support or any component thereof may be adjustable in length. In certain embodiments the support may be attached and removed by the user.

Figure 8:
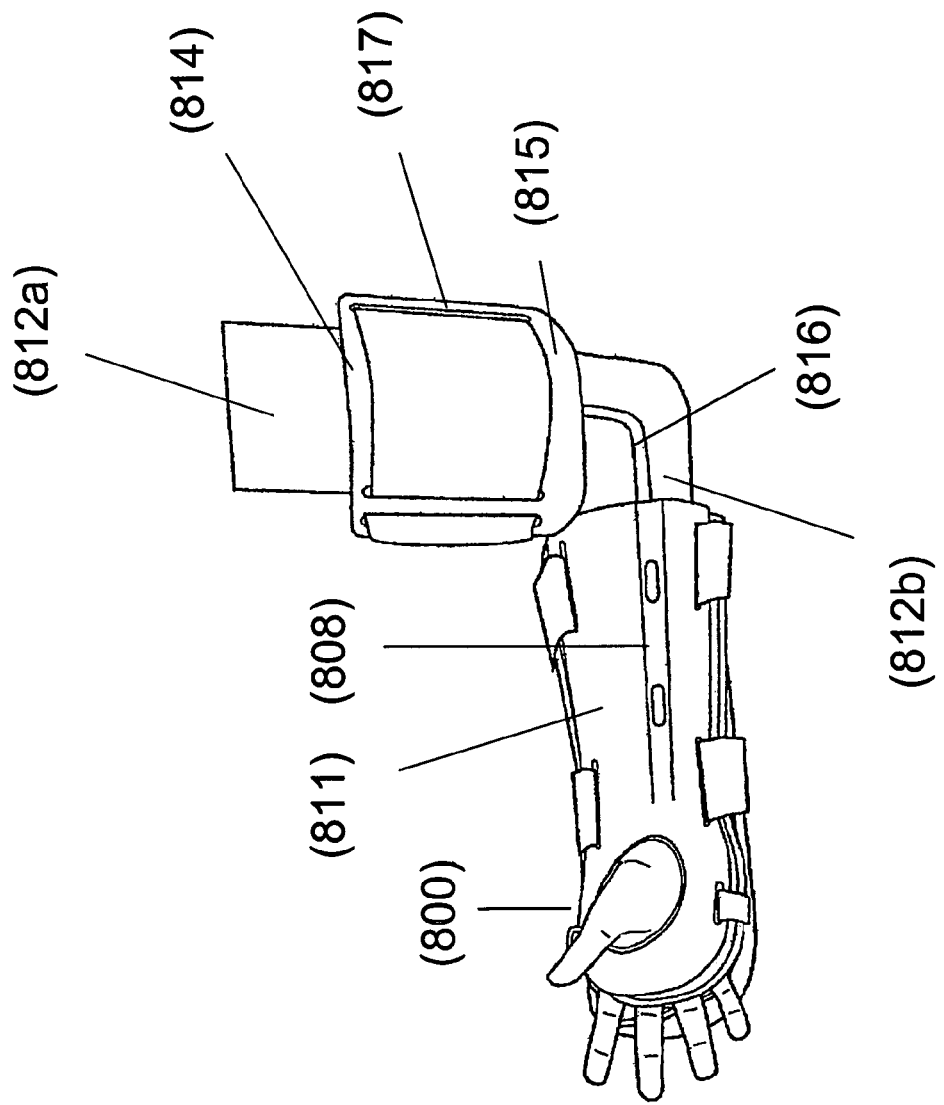
FIG. 8 depicts an embodiment of a brace and removable support applied to an injured arm.

FIG. 8 depicts an embodiment of a brace (800) having a support (817) for connecting one portion of a user's arm (812*a*) to another portion (812*b*). The support (817) may be removable and includes a bracket having plate (815) and rod (816) portions and an arm band (814). The depicted embodiment shows the bracket rod (816) affixed to a casing (811) by a slot (808) formed in the brace. In certain embodiments the casing may be articulated at the elbow joint for adding support to the injured arm.

A variety of structures may be used to achieve the desired support. In certain embodiments the brace is adapted to allow a user's thumb, fingers, toes, etc. to flex. For example, a rod may be applied across an injured limb such as being fastened to a user's forearm and to the user's hand, to impede flexion, deviation, etc. without impeding the flexibility of the thumb. In certain embodiments the user's thumb is allowed to flex freely. A brace may have a hole (618) for the thumb, as shown in FIG. 6. In certain embodiments the brace is positioned to abut at least a portion of the user's thumb and, in some embodiments, may cover a portion of the thumb. The brace may have one or more components adapted to wrap around the thumb, or to extend into contact with the fingers without making any contact with the thumb, thereby impeding rotation or flexion of the wrist without impeding flexion or rotation of the thumb.

Figure 9:
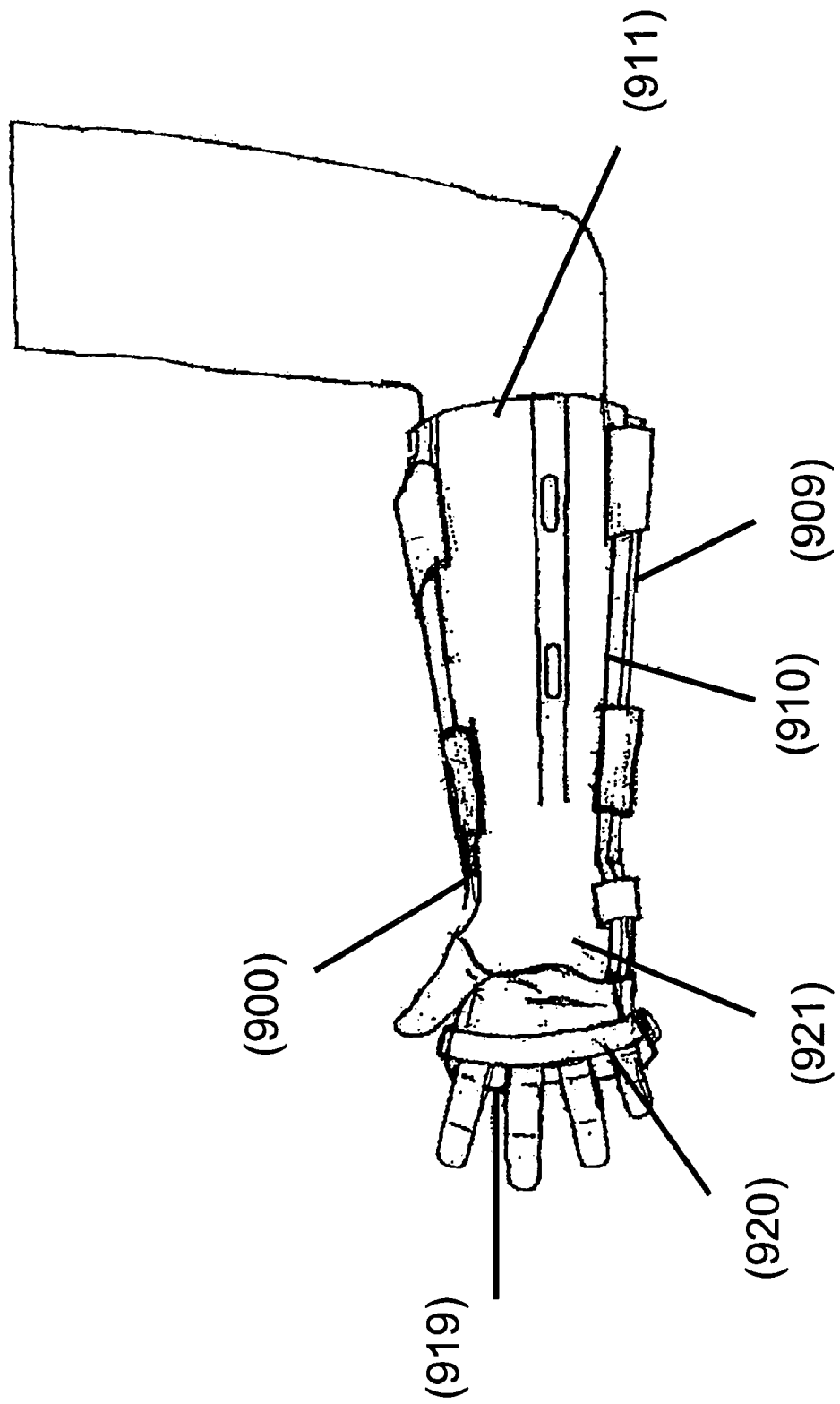
FIG. 9 depicts an embodiment of a brace attached to a user's arm, the brace having a finger strap.

Those skilled in the art will be able to envision numerous variations on the structures described herein, all of which fall within the scope of the invention. For example, FIG. 9 depicts an embodiment of a brace (900) from a medial side view. The brace extends above the wrist into contact with the thumb (921) without encircling the thumb. The brace also has a lateral side that extends to a position above the back knuckles of the fingers (919), such extension serving to impede the rotation of the wrist, and further includes a strap (920) to support the hand against the lateral portion of the brace to further impede the rotation of the wrist. A medial portion of a casing (911) is shown, as well as a medial liner (909) and a first item of compressible material (910) at least partially enclosed by the medial portion of the casing (911).

Figure 10:
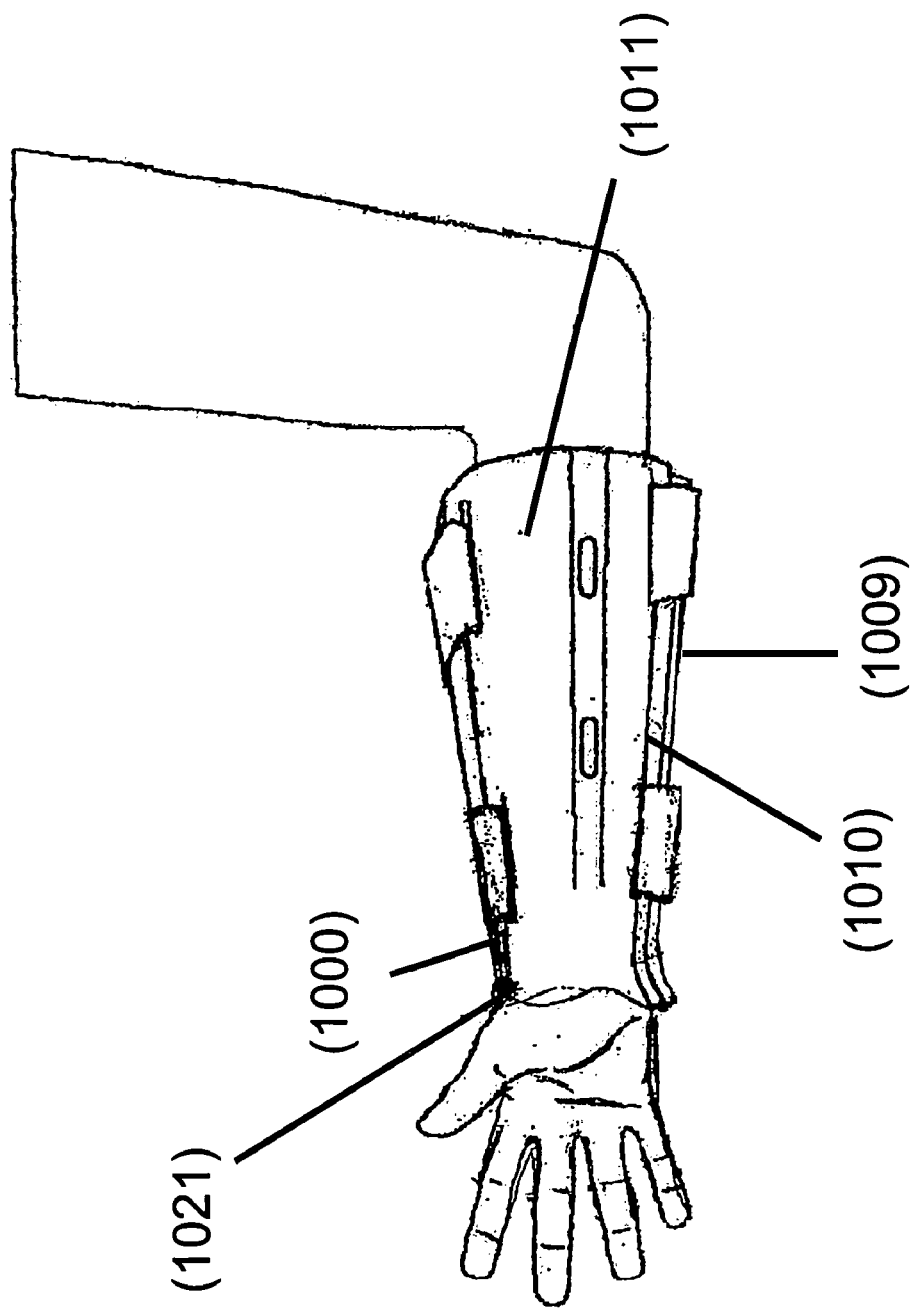
FIG. 10 depicts an embodiment of a brace extending into contact with a user's hand.

FIG. 10 depicts another embodiment of a brace (1000) from the view of the medial side thereof. The depicted brace extends above the wrist into contact with the hand (1021), such extension serving to impede the rotation of the wrist, without encircling the thumb or contacting the knuckles of the fingers on the lateral side of the brace. A medial portion of a casing (1011) is shown, as well as a medial liner (1009) and a first item of compressible material (1010) at least partially enclosed by the medial portion of the casing (1011).

Figure 11:
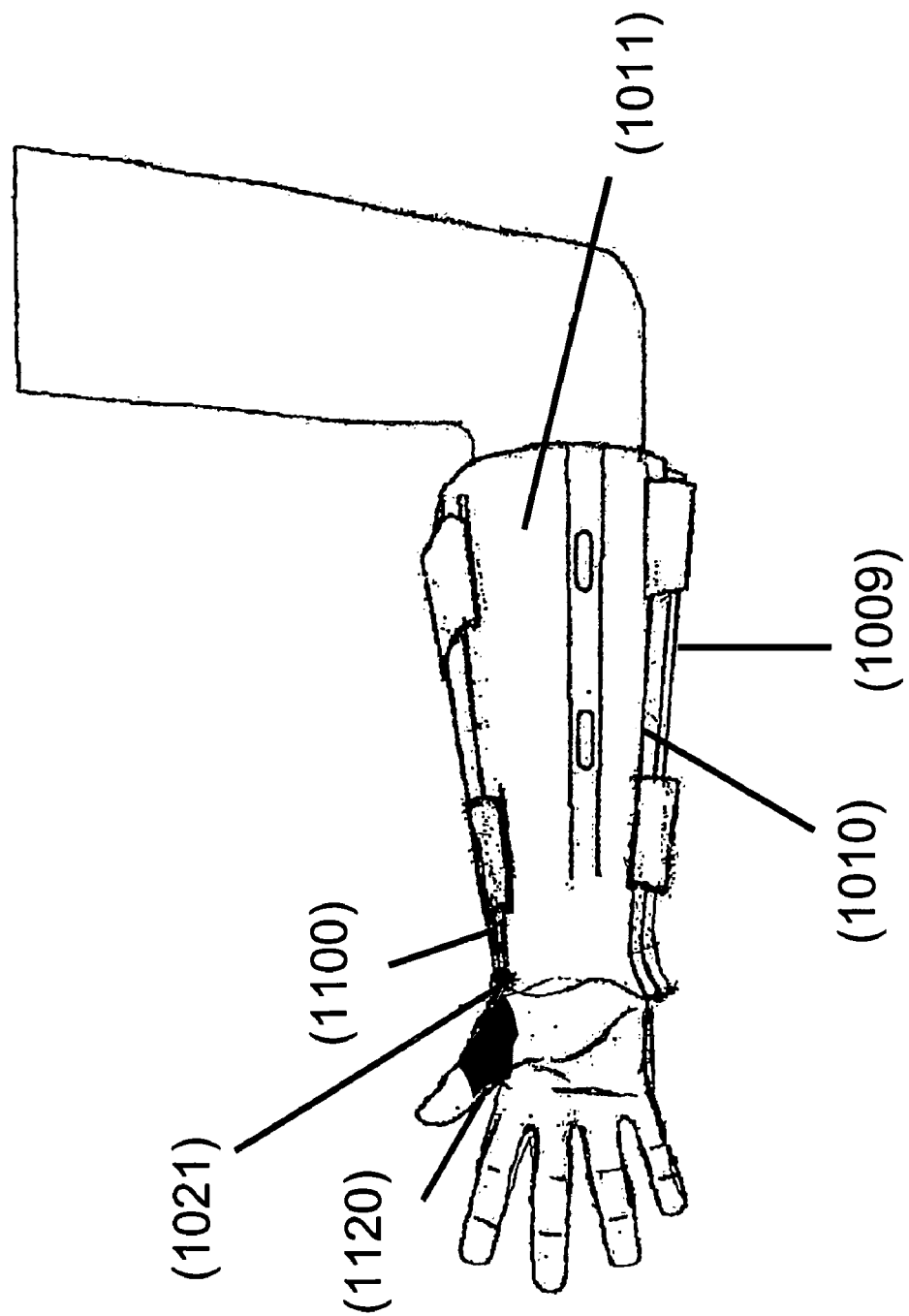
FIG. 11 depicts an embodiment of a brace with a spica for stabilizing the thumb.

FIG. 11 depicts an embodiment of a brace (1100) similar to brace (1000) with the added feature of a spica (1120) connected to the casing (1011) to further support the thumb.

Figure 12:
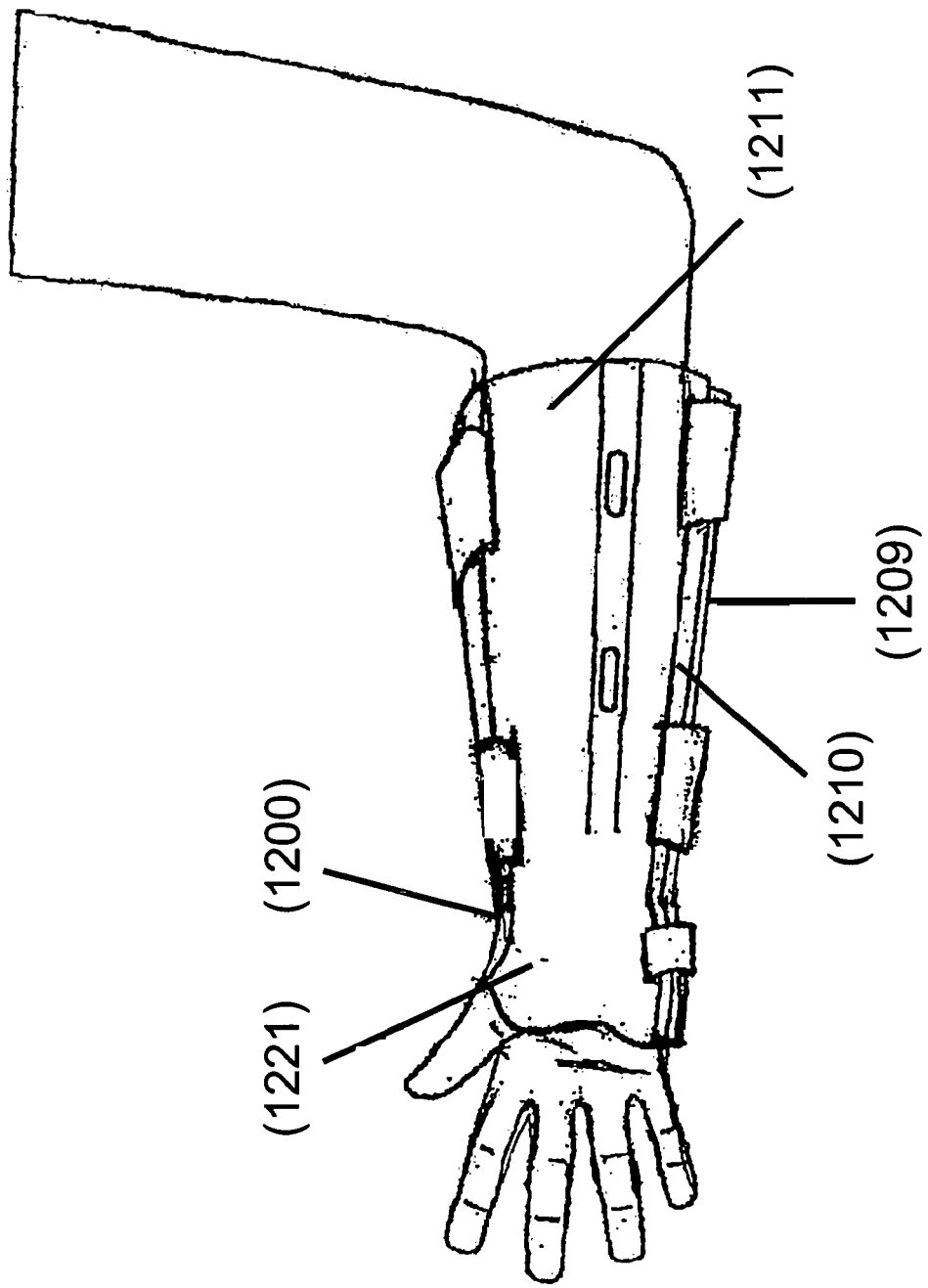
FIG. 12 depicts an embodiment of a brace extending into contact with a user's thumb.

FIG. 12 depicts another embodiment of a brace (1200) from a medial side view. The depicted brace extends above the wrist into contact with the thumb (1221) without encircling the thumb, such extension serving to impede the rotation of the wrist. A medial portion of a casing (1211) is shown, as well as a medial liner (1209) and a first item of compressible material (1210) at least partially enclosed by the medial portion of the casing (1211).

Figure 13:
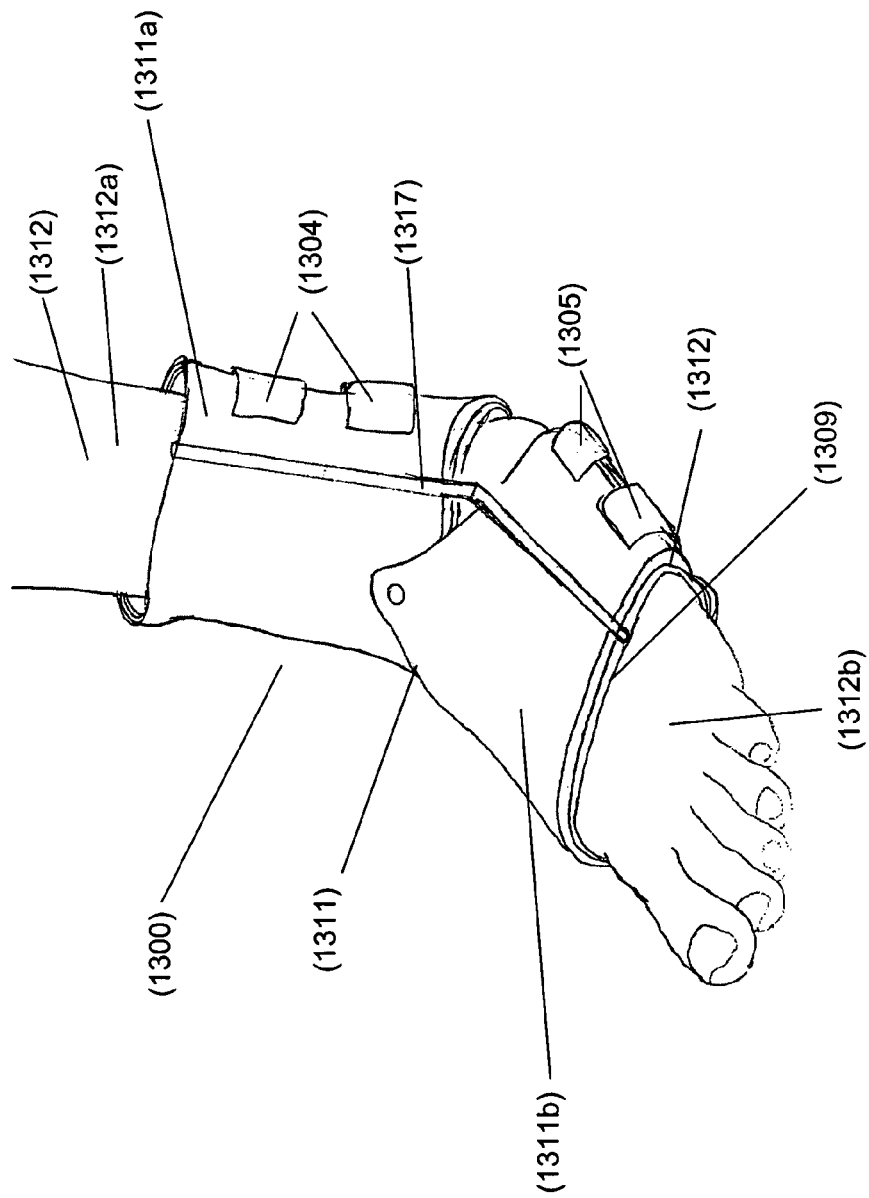
FIG. 13 depicts an embodiment of a brace applied to an injured leg.

A brace may also be adapted to treat injured legs, ankles, etc. A brace may be adapted to impede inversion, eversion, plantar flexion, and dorsal flexion of an ankle. As shown, FIG. 13 depicts an embodiment of a brace (1300), including a casing (1311) having top (1311*a*) and bottom (1311*b*) portions. Also shown is a medial liner (1309) and compressible material (1310) at least partially enclosed by the casing (1311).

The brace (1300) may be secured to a user's leg (1312) by top straps (1304) and bottom straps (1305). FIG. 13 also depicts a support (1317) for connecting one portion of a user's leg (1312*a*) to another portion (1312*b*), extending across the ankle.

Systems and methods for the use and manufacture of braces according to the invention are also contemplated. Those skilled in the art will recognize that the various features and components described herein may be readily adaptable to methods of manufacture. For example, a brace may be manufactured as an adjustable casing by providing a lateral portion comprising a casing and compressible material, providing a medial portion comprising a casing and compressible material, and providing a strap. A liner may also be provided with the lateral portion, medial portion, or both. Those skilled in the art will recognize a number of other methods of manufacture and use. For example, similar methods may be applied to manufacture braces having volar and dorsal portions. The methods for manufacturing may provide an adjustable casing that is adapted to fit across the injured limb (e.g. the wrist) and in contact with another of a user's limbs sufficient to impede flexion of the user's limb. In certain embodiments the brace is adapted to impede at least one of palmar flexion, dorsi flexion, radial deviation, ulnar deviation, pronation of the forearm, supination of the forearm. The method may be further exploited by providing compressible material, and enclosing at least part of the compressible material in the casing. In certain embodiments a brace has at least one component adapted to impede one or more of inversion, eversion, plantar flexion, and dorsal flexion of an ankle.

In another embodiment, a brace may be used to treat an injured limb. For example, an injured wrist may be treated by providing compressible material that is at least partially enclosed in an adjustable casing. The brace may have at least one component (e.g., part of the adjustable casing, a rod or other stiff item applied to the brace, etc.) adapted to fit across the wrist and in contact with a user's hand sufficient to impede at least one of palmar flexion, dorsi flexion, radial deviation, ulnar deviation, pronation of the forearm, supination of the forearm. In certain embodiments the wrist is treated by impeding palmar flexion, dorsi flexion, radial deviation, and/or ulnar deviation, without impeding pronation or supination of the forearm. Such methods typically involve fitting the casing to the user's wrist. Similarly, an injured ankle may be treated by applying compressible material enclosed (at least partially) in an adjustable casing to an ankle, the casing having at least one component adapted to impede one or more of flexion, inversion or eversion of the ankle.

The figures describe exemplary embodiments of the invention but are not limiting. One of ordinary skill in the art will understand that the braces and methods described herein can be adapted and modified for other applications, including for use with ankles, elbows, knees, or shoulders. Such additions and modifications will not depart from the scope hereof. Accordingly, the description and examples set forth herein are for illustration purposes only, and are not to be understood as limiting in any way.

The invention claimed is:

1. A brace for treating a fractured arm, comprising:
an adjustable casing having a lateral shell and a medial shell, the medial shell having a stiff component extending across the medial side of the wrist of the fractured arm, and the adjustable casing immobilizing the wrist with respect to the forearm of the fractured arm, wherein the adjustable casing includes a thumb hole protruding through the medial shell, the thumb hole comprising a first edge,
at least one inflatable cell at least partially enclosed by the lateral shell and the lateral shell extends distal to the wrist, wherein the at least one inflatable cell includes a thumb hole comprising a second edge that extends continuously around the user's thumb for the user's thumb to extend through while allowing the user's thumb to flex, and
wherein the medial shell at least partially encloses a foam pad.

2. The brace of claim 1, further comprising a mechanical fastener for tightening and loosening the casing.

3. The brace of claim 1, wherein the at least one inflatable cell includes a valve for allowing a user to selectively inflate and deflate the at least one inflatable cell.

4. The brace of claim 1, wherein the brace includes a hand-held component which applies pulsating pneumatic compression when gripped by the user.

5. The brace of claim 1, further comprising an electrical or a manual pump for adjusting fluid pressure in the at least one inflatable cell.

6. The brace of claim 5, wherein the electrical or manual pump is adapted to provide pulsating pneumatic compression to a user's wrist as the user flexes the hand.

7. The brace of claim 1, further comprising a support to impede movement of the-injured limb.

8. The brace of claim 7, wherein the support is at least one removable or unattachable rod, hinge, joint or spring.

9. The brace of claim 7, wherein the support connects a user's forearm to the user's upper arm.

10. The brace of claim 1, further comprising a spica connected to the brace for stabilizing the user's thumb.

11. The brace of claim 1, further comprising a liner adapted to be positioned between a user's wrist and the adjustable casing for absorbing moisture.

12. The brace of claim 11, wherein the liner is wicking material.

13. The brace of claim 1, wherein the brace has at least one perforation adapted to allow the user to be treated with cryotherapy without removing the brace.

14. The brace of claim 1, further comprising at least one perforation in the casing for allowing ambient air to contact the arm to ventilate the arm.

15. The brace of claim 1, wherein the inflatable cell fits across the lateral side of the user's wrist.

16. The brace of claim 15, wherein the foam pad fits across the medial side of the user's wrist.

17. The brace of claim 1, wherein the at least one inflatable cell includes a plurality of inflatable cells.

18. The brace of claim 1, wherein the inflatable cell is perimeter loaded.

19. The brace of claim 1, wherein the inflatable cell includes at least one aperture or pocket in an inner region of the inflatable cell to impede the inflatable cell from expanding in the inner region.

20. The brace of claim 1, wherein the at least one inflatable cell is compartmentalized into sub-cells to prevent an uneven expansion of the at least one inflatable cell.

21. The brace of claim 1, wherein the adjustable casing abuts at least a portion of the user's thumb with metal to immobilize the thumb.

22. The brace of claim 1, wherein a portion of the adjustable casing is being adapted to encase a scaffoid fracture.

23. The brace of claim 1, wherein the thumb hole of the at least one inflatable cell aligns with the thumb hole of the adjustable casing to create a passage for the user's thumb.

24. The brace of claim 23, comprising a liner having a thumb hole, comprising a third edge that extends continuously around the user's thumb, wherein the thumb hole of the liner aligns with the thumb holes of the adjustable casing and the at least one inflatable cell to create the passage for the thumb.

25. The brace of claim 1, wherein the thumb hole of the adjustable casing is disposed parallel to the palm of the user's hand.

26. The brace of claim 1, wherein the thumb hole of the adjustable casing is sized to expose the first metacarpal bone of the user's thumb.

27. The brace of claim 1, wherein the at least one inflatable cell is quilted or dimpled to impede the at least one inflatable cell from distributing air unevenly across the at least one inflatable cell.

28. A method for treating a fractured arm, comprising:
providing an inflatable cell that is at least partially enclosed in an adjustable stiff casing, wherein:
the adjustable stiff casing extends along a substantial portion of the fractured arm;
the adjustable stiff casing includes a thumb hole, the thumb hole comprising a first edge; and
the inflatable cell includes a thumb hole comprising a second edge that extends continuously around the user's thumb for the user's thumb to extend through while allowing the user's thumb to flex;
fitting a user's thumb through the thumb hole of the adjustable stiff casing and through the thumb hole of the inflatable cell; and
securing the adjustable stiff casing about the fractured arm.

29. The method of claim 28, wherein at least one component of the adjustable casing is adapted to impede palmar flexion, dorsal flexion, radial deviation, and ulnar deviation of a user's wrist, without impeding pronation or supination of the user's forearm.

30. The method of claim 28, wherein the adjustable casing is adapted to impede palmar flexion, dorsal flexion, radial deviation, and ulnar deviation of the user's wrist, without impeding pronation or supination of the user's forearm.

31. The method of claim 28, further comprising tightening or loosening the casing with a mechanical fastener.

32. The method of claim 28, further comprising attaching a removable support between the user's forearm and the user's upper arm.

33. The method of claim 28, further comprising positioning a moisture absorbent liner between the injured limb and the casing.

34. The method of claim 28, wherein a substantial portion of the forearm comprises at least half of the forearm.

35. The method of claim 28, wherein the pressure in the inflatable cell is adjustable to provide support for the injured arm.

36. The method of claim 28, comprising attaching metal to the adjustable stiff casing to immobilize the thumb of the fractured arm.

37. The method of claim 28, further comprising applying a stiff shell across the medial side of a user's wrist.

* * * * *